United States Patent
Arendash et al.

(10) Patent No.: US 10,765,879 B2
(45) Date of Patent: Sep. 8, 2020

(54) ELECTROMAGNETIC TREATMENT OF BRAIN AND BODY DISORDERS

(71) Applicant: NeuroEM Therapeutics, Inc., Scottsdale, AZ (US)

(72) Inventors: Gary W. Arendash, Phoenix, AZ (US); Jon W. McGarity, Scottsdale, AZ (US); Lyle R. Scritsmier, Phoenix, AZ (US)

(73) Assignee: NeuroEM Therapeutics, Inc., Phoenix, AZ (US)

( * ) Notice: Subject to any disclaimer, the term of this patent is extended or adjusted under 35 U.S.C. 154(b) by 536 days.

(21) Appl. No.: 14/205,333

(22) Filed: Mar. 11, 2014

(65) Prior Publication Data
US 2014/0257017 A1   Sep. 11, 2014

Related U.S. Application Data

(60) Provisional application No. 61/776,097, filed on Mar. 11, 2013.

(51) Int. Cl.
| | |
|---|---|
| *A61N 2/02* | (2006.01) |
| *A61N 1/40* | (2006.01) |
| *A61N 2/00* | (2006.01) |
| *A61B 5/00* | (2006.01) |
| *A61N 5/04* | (2006.01) |

(52) U.S. Cl.
CPC ............. *A61N 2/02* (2013.01); *A61B 5/4836* (2013.01); *A61N 1/40* (2013.01); *A61N 2/006* (2013.01); *A61N 5/04* (2013.01)

(58) Field of Classification Search
CPC ... A61B 18/18–1815; A61B 2018/1807–1892; A61N 2/00–12; A61N 5/02; A61N 2005/027
See application file for complete search history.

(56) References Cited

U.S. PATENT DOCUMENTS

| | | | |
|---|---|---|---|
| 6,410,137 B1 * | 6/2002 | Bunyan | C08K 5/06 428/356 |
| 6,463,336 B1 * | 10/2002 | Mawhinney | A61N 1/40 600/14 |

(Continued)

FOREIGN PATENT DOCUMENTS

| | | |
|---|---|---|
| EP | 1907052 | 1/2010 |
| EP | 1606010 | 2/2012 |

(Continued)

OTHER PUBLICATIONS

PCT; International Search Report dated Jul. 9, 2014 in Application No. PCT/US2014/023805.

(Continued)

*Primary Examiner* — Catherine B Kuhlman
(74) *Attorney, Agent, or Firm* — Fabian VanCott; Tyler M. Jeffs (57) ABSTRACT

Disclosed are devices, methods, and systems for helping to prevent (or preventing) or treat brain and/or body disorders. Embodiments of the invention have utility for enhancing cognitive function during aging. The invention utilizes electromagnetic stimulation (EMS) that can provide a range of EMS parameters and modalities. The EMS may be utilized in conjunction with physiologic sensors that can provide feedback for possible EMS modifications.

29 Claims, 3 Drawing Sheets

(56) References Cited

U.S. PATENT DOCUMENTS

| | | |
|---|---|---|
| 6,876,337 B2 | 4/2005 | Larry |
| 2004/0122281 A1* | 6/2004 | Fischell .............. A61N 2/02 600/13 |
| 2004/0127895 A1* | 7/2004 | Flock .............. A61B 18/14 606/41 |
| 2004/0176805 A1* | 9/2004 | Whelan .............. A61N 2/02 607/2 |
| 2004/0181115 A1 | 9/2004 | Sandyk et al. |
| 2004/0199070 A1* | 10/2004 | Krockel .............. A61N 1/403 600/412 |
| 2005/0228209 A1 | 10/2005 | Schneider |
| 2007/0244530 A1 | 10/2007 | Ren |
| 2008/0269851 A1* | 10/2008 | Deem .............. A61B 18/18 607/101 |
| 2009/0131739 A1* | 5/2009 | Shalev .............. A61N 1/0548 600/13 |
| 2009/0156884 A1* | 6/2009 | Schneider .............. A61N 2/02 600/14 |
| 2009/0276019 A1* | 11/2009 | Perez .............. A61N 1/403 607/115 |
| 2010/0042168 A1 | 2/2010 | Pasche et al. |
| 2010/0114086 A1 | 5/2010 | Deem et al. |
| 2010/0210894 A1* | 8/2010 | Pascual-Leone ........ A61N 2/02 600/14 |
| 2011/0230701 A1 | 9/2011 | Simon et al. |
| 2012/0065456 A1 | 3/2012 | Arendash et al. |
| 2012/0089201 A1 | 4/2012 | Pilla |
| 2012/0172954 A1* | 7/2012 | Zastrow .............. A61N 5/025 607/101 |
| 2014/0187851 A1* | 7/2014 | Cetroni .............. A61N 1/40 600/14 |
| 2014/0228620 A1 | 8/2014 | Vasishta |
| 2014/0303425 A1* | 10/2014 | Pilla .............. A61N 2/006 600/14 |

FOREIGN PATENT DOCUMENTS

| | | |
|---|---|---|
| EP | 2414038 | 2/2012 |
| WO | WO 2007044386 | 4/2007 |
| WO | WO 2008141296 | 11/2008 |

OTHER PUBLICATIONS

Gary W. Arendash, "Transcranial Electromagnetic Treatment Against Alzheimer's Disease: Why it has the Potential to Trump Alzheimer's Disease Drug Development," Journal of Alzheimer's Disease, 32 (Jun. 2012) pp. 243-266.

* cited by examiner

Figure 2

ELECTROMAGNETIC TREATMENT OF BRAIN AND BODY DISORDERS

RELATED APPLICATIONS

This application claims priority to and incorporates by reference U.S. Provisional Application No. 61/776,097, filed on Mar. 11, 2013.

FIELD OF THE INVENTION

The invention relates to devices, methods and systems that utilize electromagnetic waves (preferably of ultra-high frequency) and provide therapeutic effects for the brain and/or body and that can help prevent or prevent, ameliorate or eliminate, diseases or disorders, at least some of which are characterized by amyloid protein aggregation, mitochondrial dysfunction, and/or reduced neuronal activity. The invention also relates to devices, methods and systems for providing cognitive benefits to normal individuals, as well as to those with age-associated cognitive impairment or sub-normal cognitive function.

BACKGROUND OF THE INVENTION

A variety of both neurologic and body disorders involve abnormal amyloid protein aggregation, mitochondrial dysfunction, and/or reduced neuronal activity. Primary among amyloid-aggregating conditions in the brain is Alzheimer's Disease ("AD"), in which the protein β-amyloid (Aβ) is abnormally produced by neurons and deposited both within neurons and outside of neurons. The search for a disease-modifying drug to cure, treat or prevent AD has been ongoing, but failed to develop a drug that can prevent and/or treat AD. Other brain disorders, including those characterized by amyloid protein aggregation, for which therapeutics are currently limited or unavailable, include Mixed AD/Vascular Dementia, Cerebral Amyloid Angiopathy, Hemorrhagic Stroke, Multi-Infarct Dementia, Parkinson's Disease, Lewy Body Dementia, Down's Syndrome, Traumatic Brain Injury, Fronto-Temporal Lobe Dementia, Cerebral Traumatic Encephalopathy, Huntington's Disease, and Prion Diseases (Transmissive Spongiform Encephalopathy, Kuru, and Creutzfeldt-Jakob Disease).

AD and a number of other neurologic conditions are also characterized by mitochondrial dysfunction and/or reduced neuronal activity. Brain mitochondrial dysfunction (low ATP production) occurs in AD, Parkinson's Disease, Huntington's Disease, Amyotrophic Lateral Sclerosis (ALS), mental retardation, stroke, autism, bipolar disorder, schizophrenia, anxiety disorders, mitochondrial encephalomyopathies, epilepsy, migraine headache, and major depression. Reduced neuronal activity is characteristic of AD, stroke and various hyperkinetic disorders such as Huntington's Disease, Dystonia, and Hemiballismus.

In addition to the aforementioned neurologic conditions characterized by amyloid deposition and/or mitochondrial dysfunction, a number of body disorders also involve one or the other of these two characteristics. Abnormal amyloid deposition/aggregation is present in body disorders such as Type II Diabetes, Cardiac Amyloidosis, Systemic AL Amyloidosis, Atherosclerosis, Rheumatoid Arthritis, Aortic Medial Amyloid, and Familial Amyloid Polyneuropathy. As well, mitochondrial dysfunction is characteristic of body disorders such as Type II Diabetes, Cardiovascular Disease (including Atherosclerosis), Chronic Fatigue Syndrome, Cardiomyopathy, Coronary Artery Disease, Fibromyalgia, and Hepatitis C.

Conventional pharmacotherapy has thus far failed to slow or reverse AD adequately, and has minimally-impacted other brain/body conditions characterized by amyloidosis, mitochondrial dysfunction, and/or reduced neuronal activity. There is a need for non-pharmacologic devices, methods, and systems capable of providing effective therapeutic interventions against diseases of the brain and body—all or some having as their common features amyloid deposition, mitochondrial dysfunction, and/or reduced neuronal activity.

In relation to neurologic conditions, the field of "neuromodulation" involves techniques that can modify brain or peripheral neuronal function at one or several levels. These techniques include the following: Direct Current Stimulation (DCS), Deep Brain Stimulation (DBS), Magnetic Stimulation, and Electromagnetic Stimulation (EMS). With the exception of EMS, these neuromodulatory approaches have drawbacks that hinder their ability to address the afore-mentioned neurologic conditions. These drawbacks include (1) limited brain penetration, (2) only a focal brain area being affected by the treatment, (3) being invasive and expensive, (4) requiring clinical visits, and/or (5) having no demonstrated benefit.

In contrast to other neuromodulatory approaches against neurologic conditions, studies in AD transgenic mice and normal mice have shown an ability of EMS to prevent or reverse cognitive impairment. Among other things, these studies demonstrate the ability of EMS to: (1) prevent and reverse brain β-amyloid aggregation/deposition in vitro and in vivo, (2) enhance brain mitochondrial function, and (3) increase brain neuronal activity. Such studies are discussed in G. W. Arendash (2012) *Transcranial Electromagnetic Treatment Against Alzheimer's Disease: Why it has the potential to trump Alzheimer's Disease drug development*, Journal of Alzheimer's Disease 32: 243-266 (hereafter, "Arendash 2012"). This article is incorporated herein by reference.

Since Arendash (2012) shows that EMS enhances cognition in AD mice through anti-aggregation of amyloid proteins, mitochondrial enhancement, and increase neuronal activity, the many neurologic disorders characterized by aggregated amyloid proteins, mitochondrial dysfunction, and/or reduced neuronal activity all can potentially be improved, reversed or prevented by the use of EMS. Moreover, even normal mice respond to EMS with improved cognitive function, enhanced mitochondrial function and increased neuronal activity, indicating the potential for EMS to benefit normal subjects.

The neuromodulatory approach of EMS has thus far been limited to neurologic disorders. For example, known EMS treatments for AD only teach the use of EMS at a very high frequency and extremely low power (the power is also called the Specific Absorption Rate or "SAR") levels delivered to the ear, and for only a few seconds per session. Prior EMS work involving AD mice has been limited in providing only a specific set of EMS parameters (i.e., 918 MHz, 0.25 W/kg SAR) and a single EMS modality (i.e., GSM, pulsed and modulated), using only a single EMS-emitting antenna, and only full body treatment. For example, such a method is disclosed in U.S. Patent Publication No. 20120065456, the disclosure of which that is not inconsistent with this disclosure is incorporated herein by reference.

Given the above drawbacks of various neuromodulatory approaches, and the limited nature of the EMS work described above, a need exists for EMS devices, methods, and systems that can provide a range of EMS parameters and modalities for both the body and/or brain. This includes devices, methods, and systems to deliver full body EMS, or restricted EMS to a particular body area (e.g., the heart), and/or restricted to the brain or an area of the brain. For brain conditions/disorders, a need exists for EMS limited to the head via a self-contained device with multiple EMS emitting antennas. Such a need exists not only for such a head-only device against AD, but also against other amyloid-based neurologic conditions, as well as neurologic conditions characterized by mitochondrial dysfunction and/or reduced neuronal activity. In view of the small, but significant, loss of cognitive function/memory during normal aging (commonly called Aged-Associated Memory Impairment, or AAMI), such a head-only method to treat or prevent AAMI would be highly desirable, as would a method that could enhance cognitive function/memory in normal (unimpaired) individuals.

SUMMARY OF THE INVENTION

Aspects of the present invention include EMS devices, methods and systems for both brain- and/or body-related disorders. The invention has advantages over prior neuromodulatory approaches and known EMS methods, and can address brain and/or body disorders, including those characterized by amyloid protein deposition, mitochondrial dysfunction, and/or reduced neuronal activity.

In addition to a head-only EMS system, embodiments of the present invention may be or include a whole- or partial-body EMS system that may or may not include the head. A whole-body or partial-body system could be modifiable to provide restricted, focal EMS to a specific body area (such as the heart or knee).

Novel aspects of embodiments of the invention include: (1) a range of brain and/or body penetration profiles, from wide-spread, deep brain or body penetration to shallow penetration, to penetration of only specific regions of the brain and/or body, (2) a non-invasive device or system, (3) treatment that can be administered at a subject's home, (4) a self-contained system such that long-term daily treatment is possible, and/or (5) treatment that provides disease-modifying mechanisms of neurologic and/or bodily disorders.

One aspect of the invention that distinguishes over the prior EMS art is that a range of EMS parameters and modalities can be utilized, rather than just a single set of EMS parameters and a single modality. For example, prior EMS work involved a specific frequency of 918 MHz. The present invention covers a range of radio frequencies between 1 MHz and 25 GHz, preferably the ultra-high frequency (UHF) range of 300-3000 MHz, and most preferably within the ISM band of 902-928 MHz.

Another aspect of embodiments of the invention is that multiple EMS-emitting antennas may be employed via a head-unit device and/or body-unit device that focuses and restricts EMS to either (1) the brain or sub-regions therein, and/or (2) the body or portions thereof. As used herein, the terms "antenna(s)" or "RF antenna(s)" also include non-antenna means of generating electromagnetic waves.

Another aspect of embodiments of the invention is that the multiple antennas may be activated simultaneously or (more commonly) in sequence. In the latter case, no two antennas are simultaneously transmitting EMS on a given side of the brain. Antennas may be located at any suitable location, such as on the same side of the head or any suitable areas of the head, different sides of the head, or on one or more areas of the body. Activating antennas in sequence helps provide EMS without exceeding current FDA and FCC limits on SAR levels.

Another aspect of embodiments of the invention is that it may include a safety sensor that allows only a particular individual, such as the subject, caregiver, or medical care provider to activate it. Another aspect of embodiments of the invention is that it may automatically turn off after a specific period of EMS transmission, thus negating over-exposure of the subject. Further, embodiments of the invention may include physiologic sensors for the purpose of feedback modulation of EMS and the collection of physiologic parameters that could be impacted by EMS. The feedback may be used to modify the EMS therapy either automatically or manually. For example, collected physiologic data could be sent to data storage, and could be retrieved and used by a computer or a medical professional (either on site or at a remote location). The computer or medical professional could then make parameter modifications to a device, system, or method according to the invention, either on site or remotely.

BRIEF DESCRIPTION OF THE DRAWING

Preferred embodiments and applications of the present invention will be described with reference to the figures below.

DETAILED DESCRIPTION OF PREFERRED EMBODIMENTS

Figure 1:
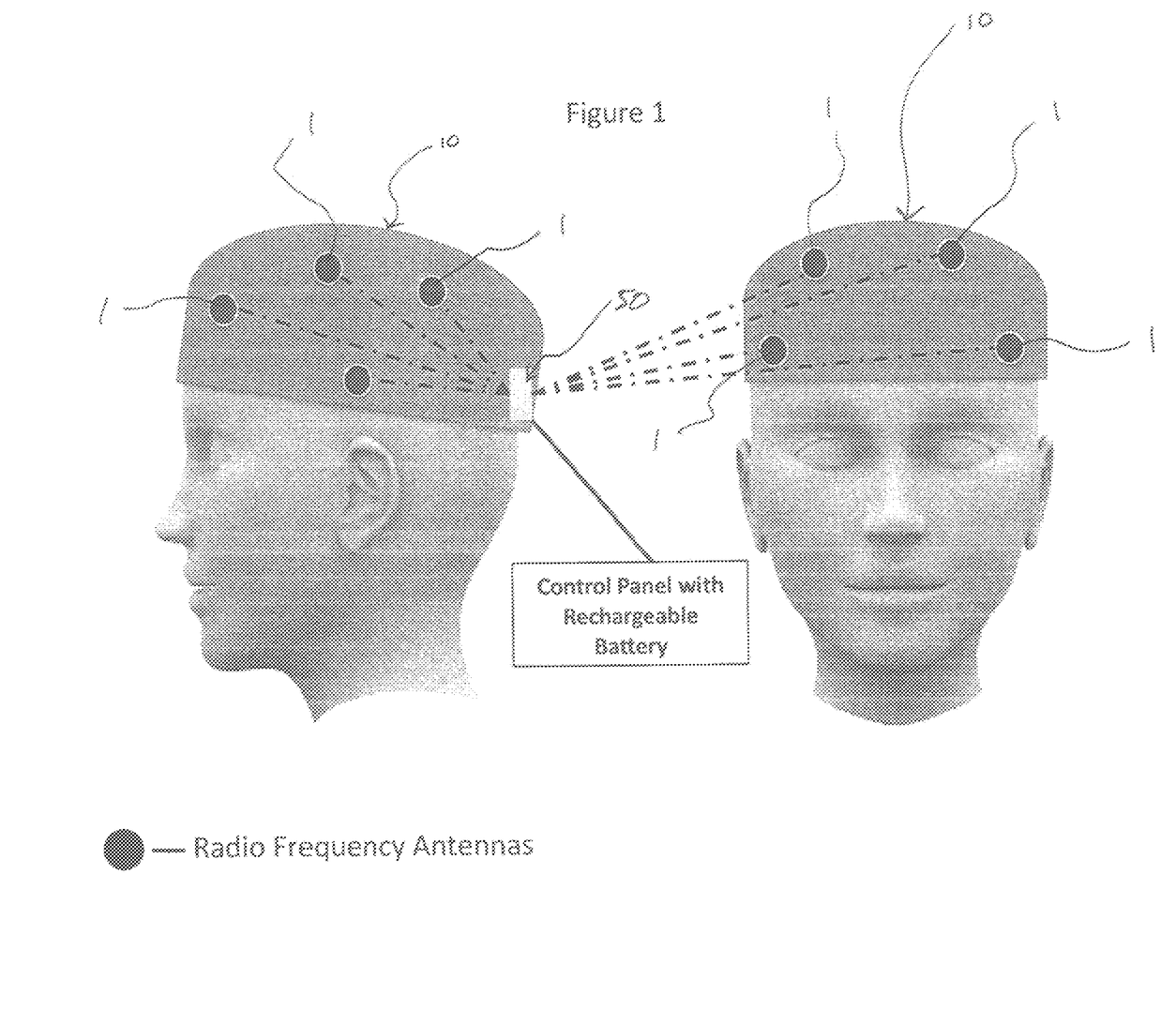
FIG. 1 illustrates a front view of an exemplary device for head-only application of ultra-high frequency EMS in frontal (left) and side views (right).

Turning now to the Figures, where the purpose is to describe preferred embodiments of the invention and not to limit same, embodiments of the invention involve devices, methods, and systems for administering radio frequency EMS to either the head alone, to the full body, to the full head and body, or to specific regions of the head and/or body. This use of EMS is believed to provide benefits through at least three mechanisms; namely, prevention/reversal of amyloid aggregation, mitochondrial enhancement, and increased neuronal activity, although the invention is not limited by any theory of operation. Turning now to FIG. 1, neurologic conditions primarily involving the brain can be treated utilizing a head-unit EMS device 10. In this example, four antennas 1 on each side of the head (or eight total) are utilized to provide EMS treatment to the forebrain. A greater or lesser number (one or more) of antennas could be incorporated into a head-unit 10, either around the head and/or over the crown, or at any desired location.

Figure 2:
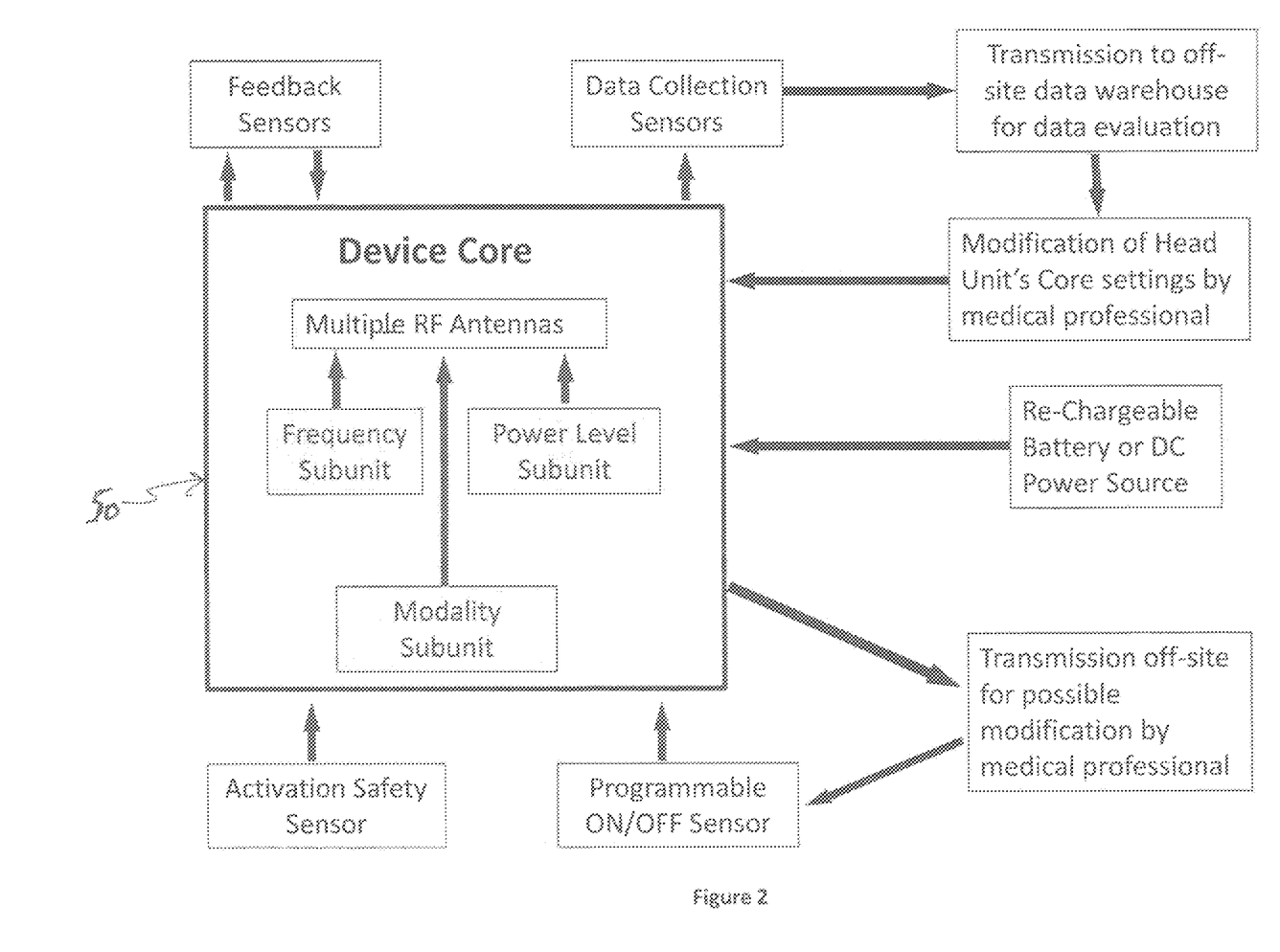
FIG. 2 is a schematic diagram of a typical ultra-high frequency EMS system for a head-only, partial-body or whole-body application. The control panel consists of three subunits (frequency, power level, and modality).

In the embodiment shown in FIGS. 1 and 2, the EMS-generating device, method and system may be utilized for preventing and treating AD. For this disease, the device may provide head-only EMS through a control panel 50 (FIG. 2) connected to an array of radio frequency (RF) antennas 1 on each side of the brain (FIG. 1). Each antenna is activated by the control panel 50, which contains controls for frequency, power level, and modality settings for each antenna 1 (FIGS. 1 and 2). Activation of the one or more antennas 1 by the control panel 50 can occur through wireless or wired connections, with both options being represented in FIG. 2 by broken lines from the control panel to the one or more antennas 1. The control panel is itself connected to a battery-based or DC-based power source other than a battery, or any other suitable power source. Each or multiple of the one or more antennas could also be connected to one another (not shown). Also within a head unit 10 according to aspects of the invention are preferably physiologic sensors connected to the control panel 50 for data collection and feedback. The head-unit 10 of this particular embodiment employs multiple antennas (one or more located on each side of the brain and/or on the top mid-line region) arrayed to provide EMS to both the cortical and sub-cortical brain areas impacted by AD. A preferred head unit will preferably have 8-16 antennas arranged to generate EMS to the cerebral cortex and sub-cortical brain areas, such as the hippocampus and entorhinal cortex.

The head unit 10 itself is preferably made of a suitably conforming material (such as cloth, nylon, microfiber, spandex) for antennas 1 to be enclosed therein and positioned in close proximity to the scalp. Alternatively, the head unit may be made to fit more loosely using a rigid helmet material (such as plastic or composite material). In addition, the head unit may contain an RF shielding material (such as a silver mesh, stainless steel mesh, or copper polyester fabric) in order to limit EMF leakage outside of the head region. RF antennas on each size of the head and/or the top mid-line region are preferably programmed to discharge EMS sequentially, such that no two antennas are simultaneously discharging EMS on the same side of the head or on the top mid-line. Alternatively, any two or more antennas 1 within the head-unit 10 may be programmed to discharge simultaneously. The nature of the transmitted EMS may be near-field, far-field, or both.

Also in this embodiment, the head unit's 10 control panel 50 can be connected to a power supply, such as a battery, located either within the head unit itself or attached to the device (but still on the person) for complete mobility during treatment and comfortable in-home treatment. If the power supply is a battery, it may be rechargeable between treatments, such as with placement of the head unit on or in a recharging device. Alternatively, the power supply can be removed or detached from head unit 10 and charged separately.

A method according to aspects of the invention comprises applying EMS through the head unit's 10 antennas 1 for therapeutic intervention over a pre-determined period of time. The system administrates EMS to the brain, which may be provided in conjunction with one or more of: (1) EMS feedback sensors to modulate treatment efficacy, (2) collection of physiologic data (such as EEG and scalp temperature) from physiologic sensors, and (3) modification of treatment on site or from a remote location, either by a computer or a medical care giver.

The EMS parameters for embodiments of the invention generally involve a frequency range from 1 MHz to 25 GHz, with a preferred frequency range of 300 to 3,000 MHz, and a most preferred frequency within the ISM band of 902-928 MHz. Embodiments of the invention also may provide an average specific absorption rate (SAR) ranging from 0.1 to 1.6 W/kg, although higher SAR levels may be used if greater utility is observed using the higher levels. The EMS signal may be continuous or non-continuous (e.g., pulsed or modulated), with the most common modality being GSM-based modulation. Other embodiments involve the EMS signal having UMTS, TETRA, or D-AMPs modulation. For all embodiments, the channel access method (which describes formats in which EMS can be delivered) could instead be TDMA or CDMA (non-pulsed).

A head-unit and/or full body or partial body device of preferred embodiments of the invention could provide EMS at any desired time intervals, such as once or multiple times daily, every other day, weekly, or any interval. Each session could be of any suitable duration, from a few seconds to a few hours to continuous. A head-unit device is usually located outside of the scalp, but may be located in whole, or part, subcutaneously, beneath the scalp, and may be permanently implanted. Similarly, a partial body device may be subcutaneously implanted in the subject.

Other aspects of the invention involve the device having a safety sensor unique to an individual, such as an individual's fingerprint, that would allow activation of the device only by the individual, which could be the subject, a caregiver, or other medical professional. Following activation of the device, the device could remain activated for a specific period of time (for example, about one hour), after which it automatically turns off and remains off until reactivated automatically or by a user. Alternatively, it could be manually turned off by the user. The device settings and intervals can be modified by a computer or medical professional, either on site or remotely through electronic transmission.

Any device, system or method according to the invention may also contain physiologic sensors for the purpose of direct feedback EMS signal modulation and/or the collection of physiologic data (such as EEG and scalp temperature). The collected data could then be saved, such as by being sent electronically to a data warehouse for evaluation by a computer or medical professional, or used for automatic adjustments to the EMS treatment. Appropriate adjustments can be made remotely or on site by a medical professional or a computer.

Another embodiment of the invention involves the same EMS method and system characteristics as described above. However, this embodiment relates to the prevention and treatment of amyloid-associated neurologic conditions other than AD, including Mixed AD/Vascular Dementia, Cerebral Amyloid Angiopathy, Hemorrhagic Stroke, Multi-Infarct Dementia, Parkinson's Disease, Lewy Body Dementia, Down's Syndrome, Traumatic Brain Injury, Fronto-Temporal Lobe Dementia, Cerebral Traumatic Encephalopathy, Huntington's Disease, and Prion Diseases (Transmissive Spongiform Encephalopathy, Kuru, and Creutzfeldt-Jakob Disease). The EMS parameters and modulation characteristics may be different for these other amyloid-associated neurologic conditions, depending on the brain areas affected. For example, the preferred embodiment of AD treatment involves an EMS profile (i.e., antenna conformation, SAR levels) that provides treatment to the entire forebrain. By contrast, a different EMS profile would be appropriate for Fronto-Temporal Lobe Dementia, wherein EMS treatment would be limited to the fronto-temporal cortex.

Another embodiment of the invention involves the same EMS device, method and system as described above, but relates to the prevention and treatment of neurologic conditions other than AD that involve mitochondrial dysfunction, including Parkinson's Disease, Huntington's Disease, Amyotrophic Lateral Sclerosis (ALS), mental retardation, stroke, autism, bipolar disorder, Schizophrenia, anxiety disorders, mitochondrial encephalomyopathies, epilepsy, migraine headache, and major depression. The EMS parameters and modulation characteristics (such as wave frequency, power level, treatment time, periodicity, and/or antenna location) may be different for these other neurologic conditions involving mitochondrial dysfunction, depending on the brain areas affected. Another embodiment of this invention involves the same EMS device, method and system as described above, but relates to the prevention and treatment of neurologic conditions other than AD that involve reduced neuronal activity, including stroke, Huntington's Disease, Dystonia, and Hemiballismus. The EMS parameters and modulation characteristics (such as wave frequency, power level, treatment time, periodicity, and/or antenna location) may be different for these other neurologic conditions involving reduced neuronal activity, depending on the brain areas affected.

Still other embodiments of the EMS device, method and system herein relate to: (1) prevention/treatment of the significant loss of short-term memory during normal aging, referred to as Age-Associated Memory Impairment (AAMI), and (2) enhancement of cognitive function/memory in normal (unimpaired) individuals and those demonstrating subnormal cognitive function/development (i.e., individuals classified as cognitively unimpaired, but within the lower levels of this classification).

Figure 3:
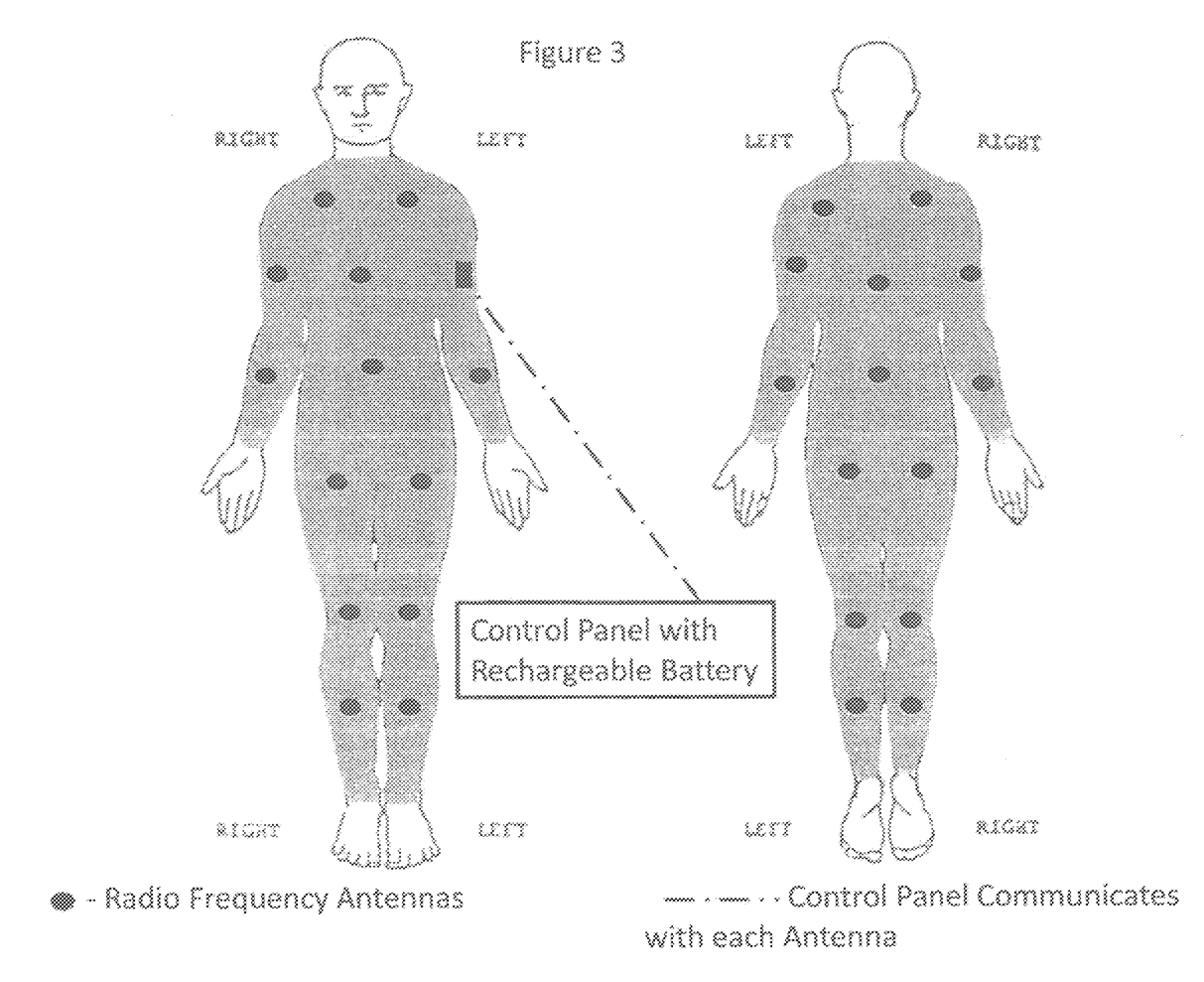
FIG. 3 illustrates both frontal and back views of an exemplary device for whole body (upper) or partial body (chest only) application of ultra-high frequency EMS.

Another embodiment of the invention relates to use of an EMS device, method and system for whole-body or partial-body treatment for prevention or treatment of various "body diseases", including those characterized by amyloid deposition or mitochondrial dysfunction. A full or partial body device or system would have the same general structure and functionality as described for the head unit 10 except that the shape, number and location of antennas, and functionality would be suited for the area and condition being treated. As shown in FIG. 3, this embodiment provides whole-body or partial-body EMS through a device worn to be in contact with the skin or in close proximity to the area requiring therapy (e.g., the chest for therapy to the heart area). The device would contain one or more RF antennas. The one or more antennas are each activated by a control panel containing wave frequency, power level, and modulation sub-units (FIG. 2) and the control panel itself is connected to a power source. This power source is preferably a battery located in the head device or on the subject, a DC source other than a battery, or any suitable power source. Also within the device are preferably physiologic sensors for data collection, transmission, and feedback. The method consists of applying EMS through the device's antenna(s) for therapeutic intervention over a pre-determined period of time and given parameter selection (i.e. wave frequency, power level, treatment time, periodicity, and/or antenna location). The system involves administration of EMS to the whole body or to a regional body area, which may be in conjunction with: (1) EMS feedback networks to modulate treatment efficacy, and/or (2) collection of physiologic data (such as skin temperature) from physiologic sensors to monitor effects of treatment or to modify treatment parameters.

For whole-body EMS, the device may be independent of the subject, such as a tube device wherein the subject lays supine or a chamber wherein the subject sits comfortably. Alternatively, whole-body EMS could be delivered by means of a body suit made of fabric such as cloth, nylon, microfiber or spandex, wherein antenna(s) would be located for close contact with the body surface. For partial-body EMS, the device may be on the skin surface with the device preferably being as close as possible to the affected body region. A suitable strap or other means of keeping the device in place over the desired body region may be used. It is possible that the device could be worn like a piece of clothing (such as a vest) or as an arm/leg wrap (such as around the knee). In addition, the whole-body or partial-body EMS fabric may contain an RF shielding material (such as a silver mesh, stainless steel mesh, or copper polyester fabric) in order to limit EMF leakage away from the body. If multiple antennas are utilized for either whole-body or partial-body EMS, they will preferably be programmed to discharge EMS sequentially, such that no two antennas are simultaneously discharging EMS into the whole body or into the partial-body region where focal EMS is being administered. Alternatively, any two or more antennas may be programmed to discharge in unison. The nature of EMS may be near-field, far-field, or both. Also in this embodiment, a battery-based power supply may be located either within the device itself or attached to the device (but preferably still on the subject) for ease of mobility during treatment and comfortable in-home treatment. The battery is preferably rechargeable between treatments.

The EMS parameters for this embodiment generally involve a frequency range from 1 MHz to 25 GHz, with a preferred frequency range of 300 to 3,000 MHz, and a most preferred frequency within the ISM band of 902-928 MHz. This embodiment also involves an average specific absorption rate (SAR) ranging from 0.1 to 1.6 W/kg, although higher SAR levels may be employed if greater utility is observed by the use of higher levels. The EMS signal may be continuous or non-continuous (e.g., pulsed or modulated), with the most common modality being GSM-based modulation. Other embodiments involve the EMS signal having UMTS, TETRA, or D-AMPs modulation. For all embodiments, the channel access method could instead be TDMA or CDMA (non-pulsed).

The intervals and timing of each EMS treatment could be the same as previously described above with respect to EMS treatment for the head.

The EMS method and system for whole-body or partial-body treatment of diseases, such as those characterized by amyloid deposition or mitochondrial dysfunction, including Type II Diabetes, Cardiac Amyloidosis, Systemic AL Amyloidosis, Atherosclerosis, Rheumatoid Arthritis, Aortic Medial Amyloid, Familial Amyloid Polyneuropathy, Cardiovascular Disease, Chronic Fatigue Syndrome, Cardiomyopathy, Coronary Artery Disease, Fibromyalgia, and Hepatitis C. The EMS parameters and modulation characteristics (i.e., wave frequency, power level, treatment time, periodicity, and/or antenna location) may differ for these body disorders involving amyloid deposition or mitochondrial dysfunction, depending on the body region(s) affected. For example, it would be anticipated that treatment of cardiac amyloidosis would involve EMS limited to the cardiac tissue, while treatment of Chronic Fatigue Syndrome (CFS) would involve whole-body EMS. This might require variations in the different parameters (i.e., wave frequency, power level, treatment time, periodicity, and/or antenna location).

Some specific non-limiting examples of the invention follow:

Example 1

A device to prevent or treat disease with electromagnetic stimulation (EMS), wherein the device comprises one or more antennas, and wherein the antennas are activated by a control panel connected to a power source.

Example 2

The device of example 1 wherein the disease is Alzheimer's Disease.

Example 3

The device of example 1 wherein the disease is one or more of the group consisting of: Mixed AD/Vascular Dementia, Cerebral Amyloid Angiopathy, Hemorrhagic Stroke, Multi-Infarct Dementia, Parkinson's Disease, Lewy Body Dementia, Down's Syndrome, Traumatic Brain Injury, Fronto-Temporal Lobe Dementia, Cerebral Traumatic Encephalopathy, Huntington's Disease, and Prion Diseases (Transmissive Spongiform Encephalopathy, Kuru, and Creutzfeldt-Jakob Disease).

Example 4

The device of example 1 wherein the disease is one or more of the group consisting of: Parkinson's Disease, Huntington's Disease, Amyotrophic Lateral Sclerosis (ALS), mental retardation, stroke, autism, bipolar disorder, Schizophrenia, anxiety disorders, mitochondrial encephalomyopathies, epilepsy, migraine headache, and major depression.

Example 5

The device of example 1 wherein the disease is one or more of the group consisting of: stroke, Huntington's Disease, Dystonia, and Hemiballismus.

Example 6

The device of either of any of examples 1-5 wherein the EMS is at an ultra-high frequency.

Example 7

The device of any of examples 1-6 wherein the antennas are within the fabric/material comprising a head unit.

Example 8

The device of example 7 wherein there is at least one antenna on the side of the head unit opposite at least one other antenna.

Example 9

The device of example 7 wherein there is at least one antenna on mid-line between the two cerebral hemispheres.

Example 10

The device of any of examples 1-6 or 8-9 wherein the antennas are RF antennas.

Example 11

The device of any of examples 1-6 or 8-10 wherein EMS is delivered without the use of an antenna.

Example 12

The device of any of examples 1-6 or 8-10 wherein the antennas may or may not be connected to one another.

Example 13

The device of any of examples 1-6, 8-10 or 12 wherein there is at least one antenna on each side of the head unit and/or over the crown of the head unit, and the antennas are arrayed bilaterally and/or on mid-line in the head unit.

Example 14

The device of any of examples 8-13 wherein the head unit is made of a suitable material, (such as cotton, nylon, polyester, spandex, or microfiber), thus allowing both comfort and functionality.

Example 15

The device of any of examples 8-14 wherein the head unit fits immediately next to the skin surface via a conforming fabric (such as those listed in the preceding example) or fits loosely via a rigid helmet (such as plastic or composite material).

Example 16

The device of any of examples 8-10 or 12-15 wherein the head unit contains a radio frequency shield material (such as a silver mesh, stainless steel mesh, or copper polyester fabric) to limit electromagnetic leakage away from the head.

Example 17

The device of any of examples 1-6, 8-10 or 12-16 wherein there is a plurality of antennas, and the antennas are programmed to discharge such that no two antennas are simultaneously discharging on the same side of the head or on mid-line.

Example 18

The device of any of examples 4-7 or 9-19 wherein any two or more antennas are programmed to discharge simultaneously on the same side of the head, or on both sides of the head, or on mid-line.

Example 19

The device of any of examples 1-7 or 9-20 wherein the one or more antennas emit one or more of the group consisting of: near-field or far-field electromagnetic transmission.

Example 20

The device of any of examples 1-18 wherein the power supply is one or more of the group consisting of: a battery or DC power from a source other than a battery.

Example 21

The device of example 20 wherein any battery-based power supply is either within the device or attached to the device.

Example 22

The device of examples 21 wherein any battery-based power supply is re-chargeable.

Example 23

The device of examples 1-22 wherein the EMS has a frequency within a range of 1 MHz to 25 GHz.

Example 24

The device of any of examples 1-23 wherein the EMS has a frequency within a range of 300 MHz and 3,000 MHz.

Example 25

The device of any of examples 1-22 wherein the EMS has a frequency of 902-928 MHz.

Example 26

The device of any of examples 1-25 wherein the range of SAR level is from 0.1 to 1.6 W/kg.

Example 27

The device of any of examples 1-25 wherein SAR levels are greater than 1.6 W/kg for average power.

Example 28

The device of any of examples 1-25 wherein the SAR level is greater than 1.6 W/kg.

Example 29

The device of any of examples 1-28 wherein the EMS signal is non-continuous.

Example 30

The device of example 29 wherein the EMS signal is pulsed.

Example 31

The device of example 29 or 30 wherein the EMS signal is modulated.

Example 32

The device of any of examples 1-28 wherein the EMS signal is continuous.

Example 33

The device of example 29 wherein the EMS signal is GSM-modulated.

Example 34

The device of any of examples 1-29 wherein the EMS signal is either UMTS-modulated, TETRA-modulated, or D-AMPs-modulated.

Example 35

The device of any of examples 1-34 wherein the EMS signal's channel access method is TDMA or CDMA (non-pulsed).

Example 36

The device of any of examples 1-35 that is located in whole, or in part, subcutaneously on the head.

Example 37

The device of any of examples 1-36 that has a safety sensor unique to an individual that would allow activation of the device only by the individual.

Example 38

The device of example 37 wherein the safety sensor is the individual's fingerprint.

Example 39

The device of any of examples 1-38 that further includes the administration of EMS in conjunction with one or more of the group consisting of: (a) EMS feedback sensors to modulate treatment, (b) sensors to collect and/or transmit physiologic data for monitoring treatment effects and modifying EMS parameters (such as wave frequency, power level, treatment time, periodicity, and/or antenna location).

Example 40

The device of any of examples 1-39 that is a whole-body device or a partial-body device.

Example 41

The device of example 40 wherein the disease being prevented or treated is one or more of the group consisting of: Type II Diabetes, Cardiac Amyloidosis, Systemic AL Amyloidosis, Atherosclerosis, Rheumatoid Arthritis, Aortic Medial Amyloid, Familial Amyloid Polyneuropathy, Cardiovascular Disease, Chronic Fatigue Syndrome, Cardiomyopathy, Coronary Artery Disease, Fibromyalgia, and Hepatitis C.

Example 42

The device of example 40 or 41 wherein the antenna(s) is an RF antenna.

Example 43

The device of example 40 or 41 wherein EMF is delivered without the use of antennas.

Example 44

The device of examples 40-42 that is either independent of the subject or in contact with the body surface via an antenna-containing body fabric.

Example 45

The device of any of examples 40-44 wherein the whole- or partial-body device is made of a suitable material such as cotton, nylon, polyester, spandex, or microfiber.

Example 46

The device of any of examples 40-45 wherein the whole- or partial-body device contains a radio frequency shield material (such as a silver mesh, stainless steel mesh, or copper polyester fabric) to limit electromagnetic leakage away from the body.

Example 47

The device of any of examples 40-46 wherein the EMS generator is on the skin surface, as close to the body region to be affected as possible.

Example 48

The device of any of examples 40-47 that includes a suitable strap or other means of keeping the device in place over the desired body region.

Example 49

The device of any of examples 40-48 that is a vest for cardiac treatment.

Example 50

The device of any of examples 40-48 that is a wrap for arm or leg MS treatment.

Example 51

The device of any of examples 40-50 wherein, if multiple antennas are utilized, they will be programmed to discharge EMS sequentially, such that no two antennas are simultaneously discharging EMS into the whole body or within the body region where focal EMS is being administered.

Example 52

The device of any of examples 40-50 wherein, if multiple antennas are utilized, any two or more antennas will be programmed to discharge EMS simultaneously.

Example 53

The devices of any of examples 40-52 wherein antennas emit either near-field or far-field electromagnetic transmission, or both.

Example 54

The devices of any of examples 40-53 wherein the power supply is a re-chargeable battery or a DC source other than a battery.

Example 55

The device of any of examples 40-54 wherein, for focal EMS of a body region, any battery-based power supply is either within the device or attached to the device, but still on the subject.

Example 56

The device of examples 40-55 wherein the EMS has a frequency of 1 MHz to 25 GHz.

Example 57

The device of any of examples 40-56 wherein the preferred range of EMS frequency is between 300 MHz and 3,000 MHz.

Example 58

The device of any of the examples 40-57 wherein the EMS has a frequency of 902-928 MH.

Example 59

The device of any of examples 40-58 where the range of SAR levels is from 0.1 to 1.6 W/kg for average power.

Example 60

The device of any of examples 40-58 wherein SAR levels are greater than 1.6 W/kg for average power.

Example 61

The device of any of examples 40-60 wherein the EMS signal is non-continuous (pulsed and modulated).

Example 62

The device of any of examples 40-60 wherein the EMS signal is continuous (continuous wave; CW).

Example 63

The device of any of examples 40-61 wherein the EMS signal is GSM-modulated.

Example 64

The device of any of examples 40-61 wherein the EMS signal is UMTS-modulated, TETRA-modulated, or D-AMPs-modulated.

Example 65

The device of any of examples 40-64 wherein the EMS signal's channel access method is TDMA or CDMA (non-pulsed).

Example 66

The device of any of examples 40-65 that has a safety sensor unique to an individual that would allow activation of the device and system only by the individual.

Example 67

The device of example 66 wherein the safety sensor senses the individual's finger print.

Example 68

The device of any of examples 1-67 wherein the device provides treatment once or multiple times daily, every other day, weekly, or any interval therein for days, weeks, or years.

Example 69

The device of any of examples 1-68 wherein any treatment session is a few seconds to a few hours to continuous.

Example 70

The device of any of examples 1-69 wherein the following activation the device will remain activated for a specific period of time, after which it automatically turns off and remains off for about 8-10 hours.

Example 71

The device of example 70 wherein the device is activated for a few seconds to a few hours to continuous.

Example 72

The device of any of examples 1-71 wherein one or more operating parameters are modified by a medical professional.

Example 73

The device of any of the examples 1-71 wherein one or more operating parameters are modified by a computer.

Example 74

The device of any of examples 72-73 wherein the parameters are modified based upon data received from EMS feedback sensors.

Example 75

The device of any of examples 1-74 that further includes one or more of: (1) EMS feedback sensors to modulate treatment, and (2) sensors to collect and/or transmit physiologic data for monitoring treatment effects and modifying EMS parameters.

Example 76

The device of any of examples 1-39 to prevent or treat Age-Associated Memory Impairment (AAMI).

Example 77

The device of any of examples 1-39 to enhance both normal and sub-normal cognition function/development.

Example 78

The device of any of examples 1-77 wherein EMS is compatible with any concurrent pharmaco-therapeutic being administered for the same neurologic or body condition.

Example 79

The device of any of examples 1-78 wherein different brain and/or body applications will involve different EMS parameters (e.g., wave frequency, power level, treatment time, periodicity, modulation format, antenna location).

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention is therefore not limited by the above described embodiment, method, and examples, but by all embodiments and methods within the scope of the appended claims and legal equivalents thereof.

What is claimed is:

1. A device to treat a human subject using electromagnetic stimulation (EMS), comprising:
   a head unit to be worn on a head region of the human subject, the head unit comprising:
   a first group of multiple antennae on a first side of the head unit; and
   a second group of multiple antennae on a second side of the head unit;
   wherein the head unit is programmed such that each of the multiple antennae in each group is configured to sequentially discharge electromagnetic waves such that no two antennae on a same side of the head discharge simultaneously;
   a power source connected to the first group and second group; and a control panel connected to the power source and configured to activate the first group and second group to discharge electromagnetic waves to create electromagnetic stimulation (EMS) in the subject's brain at a frequency of between 300 and 3,000 MHz to enhance neuronal function of neurons of the human subject.

2. The device of claim 1 wherein the first and second group each comprise RF antennas.

3. The device of claim 1 wherein the EMS is pulsed.

4. The device of claim 1 wherein the power source is a battery that is either within the device or attached to the device.

5. The device of claim 1, wherein:
   the multiple antennae are controlled by a single control panel; and
   the single control panel contains controls for frequency, power level, and modality settings for each antenna.

6. The device of claim 1, wherein multiple antennae are connected to one another.

7. The device of claim 1, wherein the control panel modulates the electromagnetic waves using at least one of GSM-based modulation, UMTS modulation, TETRA modulation, and D-AMPs modulation.

8. A method, comprising:
   providing multiple antennae on either side of a user's head via a head unit with a conforming fabric; and
   performing transcranial electromagnetic treatment (TEMT) by applying electromagnetic stimulation (EMS) to the user to enhance neuronal function of neurons of the user by:
   activating the antennae over a predetermined period of time and with given parameter selection;
   activating antennae to discharge electromagnetic waves at frequencies between 1 megahertz (MHz) and 25 gigahertz (GHz) to create the EMS in a user's brain; and
   sequentially activating antenna on either side of a brain such that no two antenna are simultaneously transmitting on a given side of the brain.

9. The method of claim 8, wherein activating antenna to frequencies between 1 megahertz (MHz) and 25 gigahertz (GHz) comprises activating antenna to frequencies between 300 and 3,000 MHz.

10. The method of claim 8, wherein activating the antenna to frequencies between 1 megahertz (MHz) and 25 gigahertz (GHz) comprises activating the antenna to frequencies between 902 and 928 megahertz (MHz).

11. The method of claim 8, further comprising automatically deactivating the electromagnetic stimulation after a specified period of time, wherein the electromagnetic stimulation remains off for just a predetermined period of time.

12. The method of claim 8, further comprising:
receiving authentication of an administering user; and
following authentication, activating the electromagnetic stimulation.

13. The method of claim 12, wherein the authentication is a biometric authentication.

14. The method of claim 8, further comprising:
collecting physiological data; and
automatically adjusting the parameters of the electromagnetic stimulation based on collected physiological data.

15. The method of claim 8, further comprising modulating the frequencies of the multiple antenna.

16. The method of claim 8, wherein applying electromagnetic stimulation to the user to enhance neuronal function of neurons of the user comprises at least one of:
activating the antennae to provide an average specific absorption rate (SAR) ranging from 0.1 to 1.6 W/kg; and
activating the antennae to provide an average specific absorption rate (SAR) greater than 1.6 W/kg.

17. The method of claim 8, further comprising selecting an electromagnetic stimulation profile based on a neurologic condition, wherein the electromagnetic stimulation profile comprises:
antenna conformation;
specific absorption rate value;
a wave frequency;
a power level;
a treatment time;
a periodicity; and
antenna location.

18. The method of claim 8, wherein applying electromagnetic stimulation to the user to enhance neuronal function of neurons of the user comprises sequentially activating antenna on either side of a brain such that two or more antennae on different sides of the head discharge simultaneously.

19. The method of claim 8, further comprising adjusting the frequency and duration of the electromagnetic stimulation to treat one or more of the following: Alzheimer's Disease (AD), Mixed AD/Vascular Dementia, Cerebral Amyloid Angiopathy, Hemorrhagic Stroke, Multi-Infarct Dementia, Parkinson's Disease, Lewy Body Dementia, Down's Syndrome, Traumatic Brain Injury, Fronto-Temporal Lobe Dementia, Cerebral Traumatic Encephalopathy, Huntington's Disease, and Prion Diseases (Transmissive Spongiform Encephalopathy, Kuru, and Creutzfeldt-Jakob Disease).

20. The method of claim 8, further comprising adjusting the frequency and duration of the electromagnetic stimulation to treat one or more of the following: Amyotrophic Lateral Sclerosis (ALS), mental retardation, stroke, autism, bipolar disorder, schizophrenia, anxiety disorders, mitochondrial encephalomyopathies, epilepsy, migraine headache, and major depression.

21. The method of claim 8, further comprising adjusting the frequency and duration of the electromagnetic stimulation to treat one or more of the following: stroke, Dystonia, and Hemiballismus.

22. The method of claim 8, further comprising adjusting the frequency and power level of the electromagnetic stimulation to treat Age-Associated Memory Impairment (AAMI).

23. The method of claim 8, further comprising modulating the electromagnetic stimulation to enhance normal cognition function.

24. The method of claim 8, further comprising activating the multiple antennae multiple times per day.

25. A method, comprising:
providing transcranial electromagnetic treatment (TEMT) by:
determining an electromagnetic stimulation (EMS) profile based on an affected brain area and a neurological condition to be treated, wherein the EMS profile comprises:
a specific absorption rate value between 0.1 to 1.6 W/kg;
a wave frequency between 1 megahertz (MHz) and 25 gigahertz (GHz);
a power level;
a treatment time; and
a periodicity;
providing multiple antennae on either side of a user's head via a head unit; and
applying EMS to a sub-cortical brain area of the user to enhance neuronal function of neurons of the user, ameliorate amyloid protein aggregation, and enhance mitochondrial energy production by:
activating the antennae to discharge electromagnetic waves to a user's brain over a predetermined period of time based on the EMS profile; and
sequentially activating antenna from arrays on either side of a brain such that no two antenna are simultaneously transmitting on a given side of the brain.

26. The method of claim 25, further comprising:
collecting physiological data; and
automatically adjusting the frequency and power level of the EMS based on collected physiological data to ameliorate amyloid protein aggregation, enhance mitochondrial energy production, and increase neural activity.

27. The method of claim 26, wherein collected physiological data is selected from the group consisting of electroencephalogram data and scalp temperature.

28. The method of claim 25, wherein:
applying EMS to the user comprises activating the antennae multiple times during a particular interval; and
the method further comprises:
deactivating the multiple antennae after a period of time; and
maintaining the multiple antennae deactivated for a predetermined period of time.

29. The method of claim 25, wherein:
the EMS profile comprises an EMS modality selected based on an affected brain area and a neurological condition to be treated; and
the EMS modality is selected from the group consisting of GSM-based modulation, UMTS modulation, TETRA modulation, and D-AMPs modulation.

* * * * *